United States Patent
Sage et al.

[11] Patent Number: 6,017,606
[45] Date of Patent: *Jan. 25, 2000

[54] REUSABLE MULTICOMPARTMENT THERMAL COMPRESS

[75] Inventors: Linda Sage; Don Sage, both of Armonk, N.Y.

[73] Assignee: Danscott Enterprises, Armonk, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/857,196

[22] Filed: May 15, 1997

[51] Int. Cl.[7] ....................................................... B32B 3/12
[52] U.S. Cl. ............................... 428/68; 428/71; 428/72; 428/102; 428/167; 428/168; 428/192; 602/75; 602/76; 602/78; 607/108; 607/114
[58] Field of Search ................................. 428/68, 71, 72, 428/73, 74, 76, 102, 192, 167, 168; 206/484.1, 484.2; 602/75, 76, 78; 608/108, 109, 110, 111, 114

[56] References Cited

U.S. PATENT DOCUMENTS

| | | | |
|---|---|---|---|
| 4,780,117 | 10/1988 | Lahey | 62/4 |
| 4,865,012 | 9/1989 | Kelley | 604/291 |
| 4,897,297 | 1/1990 | Zafiroglu | 428/102 |
| 4,910,978 | 3/1990 | Gordon | 62/530 |
| 5,150,707 | 9/1992 | Anderson | 604/368 |
| 5,194,315 | 3/1993 | Itoh | 428/72 |
| 5,248,709 | 9/1993 | Breham | 523/221 |
| 5,391,198 | 2/1995 | Cheney, III | 607/114 |
| 5,405,671 | 4/1995 | Kamin | 428/72 |
| 5,461,085 | 10/1995 | Nagatomo | 521/183 |
| 5,534,020 | 7/1996 | Cheney, III | 607/108 |
| 5,709,089 | 1/1998 | Dawson et al. | |

OTHER PUBLICATIONS

Information concerning Terra–Sorb SuperAbsorbent Polymers from Industrial Services International, Inc. Web Site, dated as early as May 5, 1997.

*Primary Examiner*—Nasser Ahmad
*Attorney, Agent, or Firm*—Amster, Rothstein & Ebenstein

[57] ABSTRACT

The present invention is directed to a reusable thermal pack that comprises a bag formed of a water-permeable fabric defining a plurality of laterally adjacent compartments, and a superabsorbent polymer disposed in the bag compartments, wherein the polymer forms a gel in the presence of an aqueous solution, and the bag compartments are gel-retainable. The thermal pack of the present invention can be applied as a cold or hot compress for medicinal purposes, and also as an aid for cooling down following exercise. The thermal pack of the present invention, once hydrated in the presence of the aqueous solution, becomes cool and stays cool for several days without refrigeration, and can be made cooler if chilled in the refrigerator or freezer, or warmed if placed in the microwave, if desired.

19 Claims, 2 Drawing Sheets

REUSABLE MULTICOMPARTMENT THERMAL COMPRESS

BACKGROUND OF THE INVENTION

The present invention relates to a reusable multicompartment thermal pack comprising a bag formed of a water-permeable fabric defining a plurality of laterally adjacent compartments, and a superabsorbent polymer disposed in the bag compartments.

Thermal packs that can be chilled or heated for use as cold and hot compresses, respectfully, are well known in the prior art. For example, the most widely used thermal packs in the prior art are hot water bottles or ice bags made of rubber or plastic material. However, the problem with such packs is that they generally tend to be cumbersome, weighty and are not particularly useful for travel.

Other typical thermal packs in the prior art contain water, gel or other ingredients that permit the packs to be chilled or heated, and then applied to the desired area. For example, Kelley, U.S. Pat. No. 4,865,012, issued Sep. 12, 1989, describes such a reusable thermal pack that comprises a mixture of water, salt, cellulose and flour sealed in a pliable bag, that can be chilled or heated as desired. Gordon, et al., U.S. Pat. No. 4,910,978, issued Mar. 27, 1990, describes a reusable thermal pack comprising a gel-like substance in a plastic bag containing a fabric outer layer. However, the problem with such packs is that because they always contain water or gelled material, they tend to be cumbersome, weighty and take up a great deal of storage space.

In addition to the aforementioned packs, other packs are known in the prior art. For example, Anderson, U.S. Pat. No. 5,150,707, issued Sep. 29, 1992, describes a hot/cold thermal pack that contains an absorbent package having a gel-forming synthetic resin in particulate form deposited on an adhesive-coated substrate disposed between a pair of fibrous non-woven porous filter layers and covered on the outside by a pair of paper-like plies of nonwoven porous absorbent material. However, when the Anderson pack is exposed to water, the adhesive coating dissolves thus rendering the Anderson pack non-reusable. In addition, the Anderson pack is complex to manufacture.

Lahey, et al., U.S. Pat. No. 4,780,117, issued Oct. 25, 1988, describes a time-release cooling pack having a first compartment containing solid reactant particles coated with a reaction delaying penetrable coating and a second compartment containing a liquid which reacts with the solid reactant in an endothermic reaction. However, like the Anderson pack, the Lahey pack is not reusable, and in addition, can only be used as a cold pack.

Cheney, et al., U.S. Pat. No. 5,391,198, issued Feb. 21, 1995, describes a hot/cold thermal compress that comprises a water porous fabric bag containing a dehydrated water soluble acrylic polymer and a thickening agent to enhance the water absorption of the polymer. However, because the Cheney compress utilizes a water soluble polymer, a portion of the polymer will invariably be released from the compress when in contact with water, resulting in an unpleasant feel to the user, and also limiting the useful life of the compress. In addition, the Cheney compress requires the use of a thickening agent to enhance the water absorption of the polymer. A variation of this pack is also described in Cheney, et al., U.S. Pat. No. 5,534,020, issued Jul. 9, 1996, where ammonium nitrate or calcium chloride replace the thickening agent, and a separate, enclosed bag of water is also included within the pack.

Zafiroglu, U.S. Pat. No. 4,897,297, issued Jan. 30, 1990, describes a compress that comprises two outer layers surrounding a particulate filling material made of 5–30% of a superabsorbent polymer and 70–95% of a diluent such as wood pulp. At least one of the outer layers is a water-permeable, elastic fabric. The Zafiroglu Patent, however, teaches that concentrations of superabsorbent polymer greater than 30% should be avoided because at such concentrations, the filling material does not wet uniformly, may even block after absorbing but a small about of water, and its water-holding capacity per unit weight starts diminishing with further increases in concentration.

SUMMARY OF THE INVENTION

The present invention is directed to a reusable thermal pack that comprises a bag formed of a water-permeable fabric defining a plurality of laterally adjacent compartments, and a superabsorbent polymer disposed in the bag compartments, wherein the polymer forms a gel in the presence of an aqueous solution, and the bag compartments are gel-retainable. The pack of the present invention, once hydrated in the aqueous solution, becomes cool and stays cool for several days without refrigeration, and can be made cooler if chilled in the refrigerator or freezer, or warmed if placed in the microwave, if desired.

The thermal pack of the present invention can be applied as a cold or hot compress for medicinal purposes, and also as an aid for cooling down following exercise. In this connection, the pack of the present invention can be designed in any manner that facilitates the application of the pack to desirable body parts such as the neck, head, arms, elbows, wrists, legs, thighs, knees, calves, ankles, feet and the like. Unlike many prior art thermal packs, the pack of the present invention also is easy to manufacture, can be reused as often as desired, and when dehydrated, is lightweight and takes up little space, rendering the pack readily storable, and useful in travel.

In addition to these advantages, the thermal pack of the present invention, by containing a plurality of laterally adjacent compartments, promotes better surface area and a more uniform distribution of the gel than a pack of similar size having only a single compartment. The multicompartment pack of the present invention is also less voluminous and therefore requires less polymer than a pack of similar size having a single compartment. Since the multiple compartments are less voluminous and also require less polymer, the thermal pack of the present invention, when hydrated, is also less bulky, weighty and cumbersome than a similar size pack having only a single compartment.

DETAILED DESCRIPTION OF THE INVENTION

Figure 1:
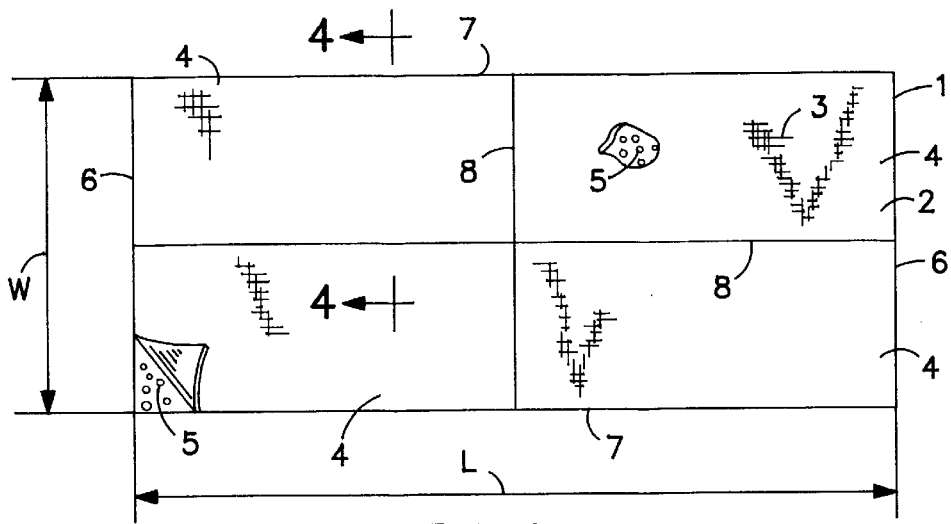
FIG. 1 is a top view of the thermal pack of the present invention.
Figure 2:
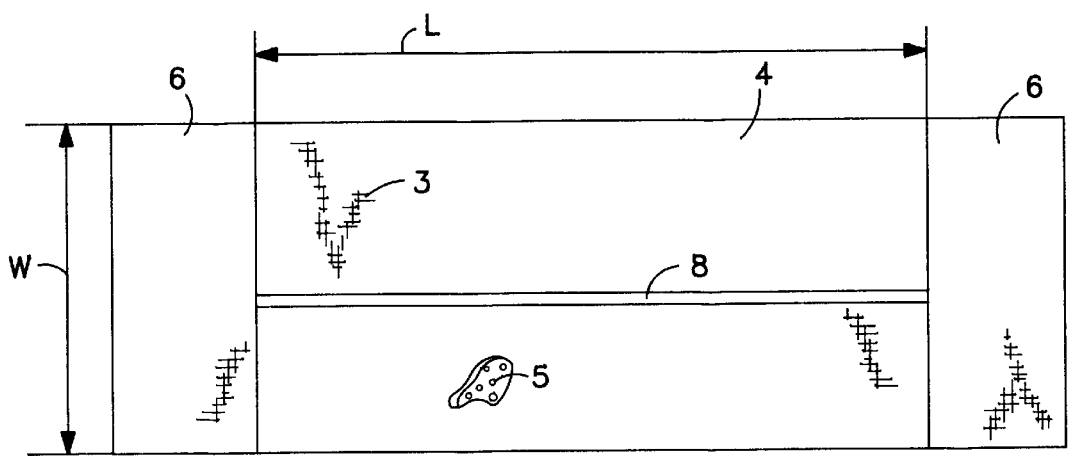
FIG. 2 is a top view of another embodiment of the thermal pack of the present invention.

Referring now to FIG. 1, the thermal pack (1) of the present invention comprises a bag (2) formed of a water-permeable fabric (3) defining a plurality of laterally adjacent compartments (4), and a superabsorbent polymer (5) disposed in the bag compartments (4). As shown in FIGS. 1 and 2, the pack of the present invention may have a pair of longitudinally spaced end portions (6) defining a length L therebetween, and a pair of traversely spaced edges (7) defining a width W therebetween.

The bag compartments may be prepared from a single piece of fabric or a plurality of fabric pieces. The fabric should be water-permeable in the sense that water can penetrate the fabric causing the superabsorbent polymer to absorb moisture, and as the superabsorbent polymer releases moisture over time, permit the moisture to slowly evaporate through the fabric. The bag compartments should be gel-retainable in the sense that the gel formed in the presence of the aqueous solution stays contained within the bag compartments and does not penetrate through the fabric or into other bag compartments under normal soaking conditions. In the preferred embodiment, the fabric is made of nylon or similar material that is not only water-permeable and gel-retainable, but also permits good transfer of cold or heat from the gel to user, is not susceptible to mildew, and dries quickly.

Figure 3:
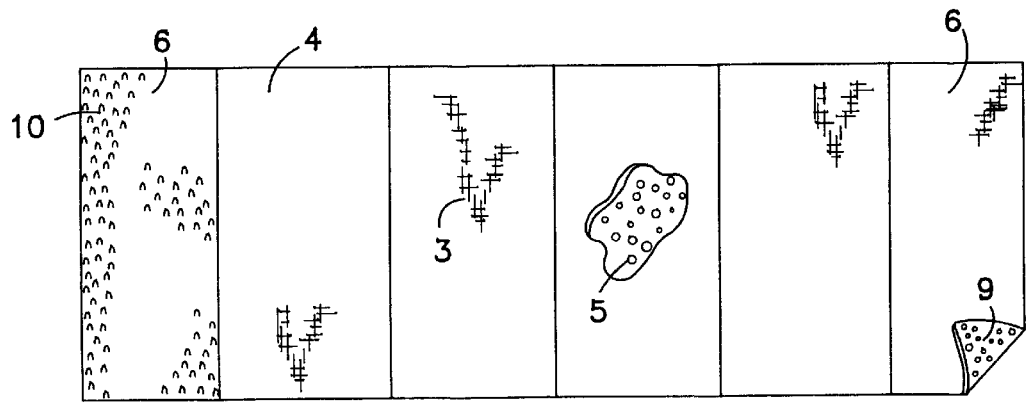
FIG. 3 is a top view of another embodiment of the thermal pack of the present invention.

"Laterally adjacent" means that the bag compartments are on the same plane and side-by-side although not necessary connected to one another. The bag compartments may be arranged in any manner so long as the majority of the surface area of the pack possesses bag compartments containing the superabsorbent polymer. By way of a non-limiting example, as shown in FIG. 1, the bag compartments may include two sets of parallel, longitudinally extending compartments (4). The bag compartments also may included two longitudinally extending compartments (4) that extend between the pair of longitudinally spaced end portions as shown in FIG. 2, or include four parallel, traversely extending compartments (4), each of which extends between the pair of traversely spaced edges as shown in FIG. 3. Other variations would be apparent to one skilled in the art. The bag compartments (4) may be separated by a bag compartment separator such as a single seam (8) as shown in FIG. 1, or a plurality of seams (8) defining an area devoid of superabsorbent polymer as shown in FIG. 2. The seams may be stitched, heat sealed, and the like.

Figure 5:
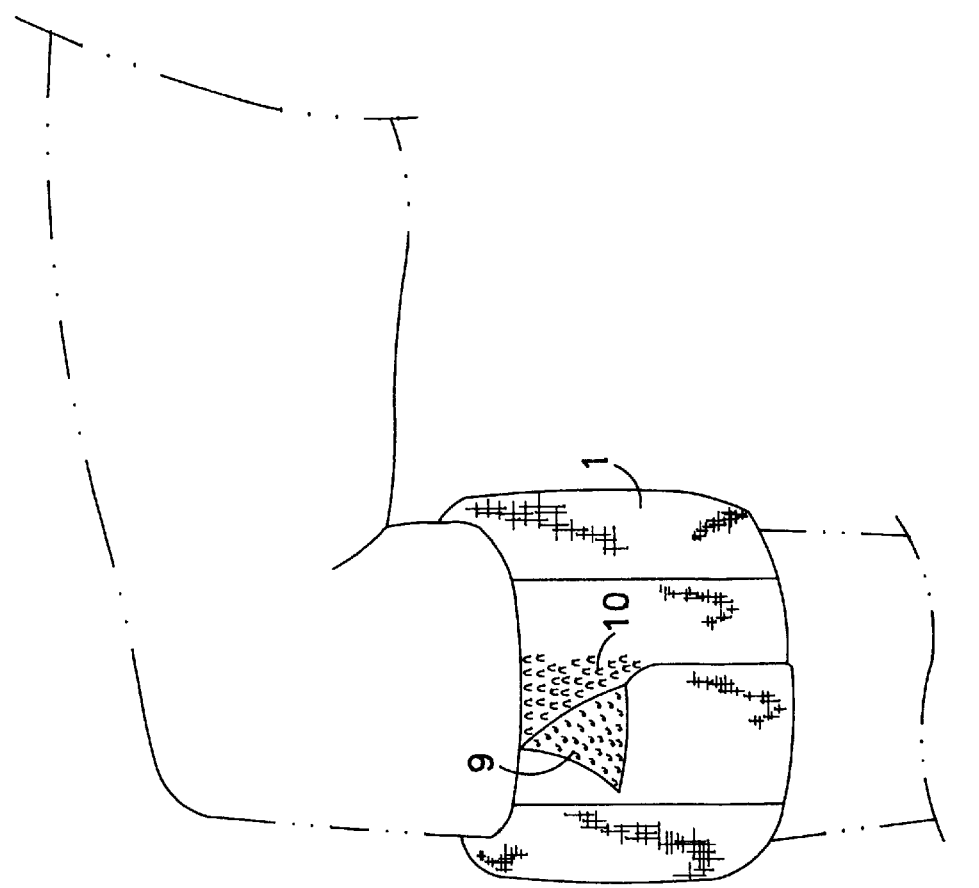
FIG. 5 represents the thermal pack of the present invention being worn on the leg of a user.
Figure 4:
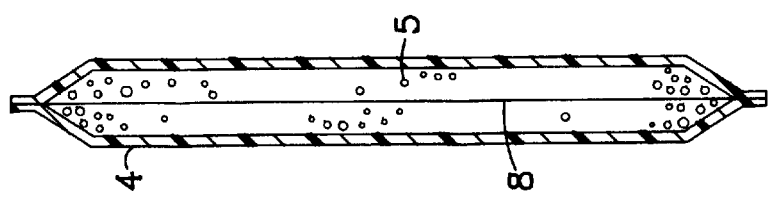
FIG. 4 is a cross-sectional view of the thermal pack shown in FIG. 1.

Depending on the proposed use of the pack, the pair of longitudinally spaced end portions (6) may be the end of the bag compartments as shown in FIG. 1, or a separate area devoid of superabsorbent polymer as shown in FIG. 2. If the pack is to be used as a cooling device for putting around the neck, for example, the spaced end portions may comprise material that can be used for handling the pack such as fabrics made of cotton, nylon or some other material, and may also include a filler such as a polyester filler and the like. If the pack is to be used as a thermal pack for medicinal purposes, for example, the spaced end portions (6) also may comprise elements of a mating system such as hooks (9) and fabric (10) of Velcro as shown in FIG. 3, or other mating systems known in the art, and applied as shown in FIG. 5.

As used herein, a "superabsorbent polymer" is a dry, water-insoluble crystal-like polymer that is capable of absorbing and storing many times its weight in moisture, that slowly releases the moisture over time. Preferably, the superabsorbent polymer is in the form of crystalline granules having particle sizes that are sufficiently large (e.g. about 1 mm to about 3 mm) to prevent any loss of the dry polymer from the bag compartments. Suitable superabsorbent polymers preferably include superabsorbent polymers that are capable of absorbing at least a hundred times their weight in water, and preferably about 300–400 times their weight in water, such as the superabsorbent polymer sold under the trade name TERRA-SORB AG (a cross-linked anionic acrylic polymer) by Industrial Services International, Bradenton, Fla. However, other commercially available superabsorbent polymers can be used. The amount of dry, superabsorbent polymer present in the bag compartments will depend upon the volume of the bag compartments and the degree of absorption of the superabsorbent polymer. However, it is generally preferred that the superabsorbent polymer is disposed in the bag compartments in an amount effective to promote uniform distribution of the gel in the presence of a sufficient quantity of an aqueous solution.

To facilitate the use of the pack of the present invention, the pack is soaked in an aqueous solution such as water for a period of time until the superabsorbent polymer in the bag compartments is hydrated to the desired amount. It is generally preferred that the superabsorbent polymer should not be over hydrated causing the gel to expand through the bag compartments. However, if over hydration occurs, the polymer can be removed from the surface of the pack by washing the pack with soap and water. Since over hydration is more prone to occur during the first soaking, it may be desirable although not necessary to incorporate soap in the aqueous solution to facilitate the removal of any polymer that may be released from the pack due to over hydration. Once hydrated in the aqueous solution, the pack becomes cool and stays cool for several days without refrigeration. If a cooler pack is desirable, the pack may be chilled in the refrigerator or freezer, or some other cooling means. If the pack is to be used as a heat compress, the pack may be heated in the microwave, and the like.

The pack of the present invention may be designed to be in a variety of shapes and sizes. When the pack is to be used for draping around the neck, for example, the pack may be shaped like a scarf. The pack shown in FIG. 2, if extended longitudinally, can be used in such a manner. For application to other parts of the body, it may be desirable that the traverse edges of the pack be designed to allow a more comfortable wearing of the pack (e.g. curved edges).

All patents mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A reusable thermal compress for application to a human or animal body part comprising a bag consisting essentially of a water-permeable fabric defining a plurality of laterally adjacent compartments, and a superabsorbent polymer disposed in the bag compartments, wherein the polymer forms a gel in the presence of an aqueous solution, the bag compartments are gel-retainable and the reusable thermal compress is configured and dimensioned for application to the body part.

2. The compress of claim 1, having a pair of longitudinally spaced end portions defining a length L therebetween, and a pair of traversely spaced edges defining a W therebetween.

3. The compress of claim 2, wherein the bag compartments are separated by a bag compartment separator.

4. The compress of claim 3, wherein the bag compartment separator is a seam or a plurality of seams defining an area devoid of superabsorbent polymer.

5. The compress of claim 2, wherein the bag compartments include a plurality of longitudinally extending compartments.

6. The compress of claim 5, wherein each of the longitudinally extending compartments extend between the pair of longitudinally spaced end portions.

7. The compress of claim 5, wherein the longitudinally extending compartments are parallel.

8. The compress of claim 2, wherein the bag compartments include a plurality of traversely extending compartments.

9. The compress of claim 8, wherein each of the traversely extending compartments extend between the pair of traversely spaced edges.

10. The compress of claim 8, wherein traversely extending compartments are parallel.

11. The compress of claim 2, where in the longitudinally spaced end portions are devoid of superabsorbent polymer.

12. The compress of claim 11, wherein the longitudinally spaced end portions comprise elements of a mating system.

13. The compress of claim 1, wherein the water-permeable fabric is nylon.

14. The compress of claim 1, wherein the superabsorbent polymer absorbs at least 100 times it weight in water.

15. The compress of claim 1, wherein the superabsorbent polymer is in the form of crystalline granules.

16. The compress of claim 1, wherein the superabsorbent polymer is disposed in the bag compartments in an amount effective to promote uniform distribution of the gel in the presence of a sufficient quantity of an aqueous solution.

17. A reusable thermal compress for application to a human or animal body part consisting essentially of a water-permeable nylon fabric defining a plurality of laterally adjacent bag compartments, and a superabsorbent polymer disposed in the bag compartments, wherein the polymer forms a gel in the presence of an aqueous solution, the superabsorbent polymer absorbs at least 100 times it weight in water, and the reusable thermal compress is configured and dimensioned for application to the body part.

18. The compress of claim 17, where the superabsorbent polymer absorbs 300–400 times it weight in water.

19. The compress of claim 17, which further comprises elements of a mating system.

* * * * *